(12) United States Patent
Ulman et al.

(10) Patent No.: US 6,962,964 B2
(45) Date of Patent: Nov. 8, 2005

(54) HYDROGENATION OF METHYLENEDIANILINE HOMOLOGS AND EPOXY RESINS CURED WITH SAME

(75) Inventors: Michael Ulman, Alburtis, PA (US); Gamini Ananda Vedage, Bethlehem, PA (US); David Alan Dubowik, Allentown, PA (US); Stephen Michael Boyce, Bath, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 185 days.

(21) Appl. No.: 10/359,450

(22) Filed: Feb. 6, 2003

(65) Prior Publication Data

US 2004/0162409 A1 Aug. 19, 2004

(51) Int. Cl.⁷ .............................................. C08G 59/00
(52) U.S. Cl. ...................... 528/122; 525/406; 528/123; 528/124; 528/407; 564/305; 564/306; 564/315; 564/330; 564/448; 564/451; 564/457; 564/462
(58) Field of Search ....................... 525/510; 528/122, 528/123, 124, 407; 564/305, 306, 426, 451, 457

(56) References Cited

U.S. PATENT DOCUMENTS

| | | | |
|---|---|---|---|
| 2,817,644 A | 12/1957 | Shokal et al. ................. | 260/47 |
| 2,981,711 A | 4/1961 | Meyer et al. ............... | 260/31.2 |
| 3,351,610 A | 11/1967 | Preininger et al. ............ | 260/47 |
| 3,636,108 A | 1/1972 | Brake ..................... | 260/563 D |
| 3,959,374 A | 5/1976 | Brennan et al. ......... | 260/563 B |
| 4,226,737 A | 10/1980 | Kluger et al. ............... | 252/182 |
| 4,321,353 A | 3/1982 | Kluger et al. ............... | 528/120 |
| 4,447,586 A | 5/1984 | Shimp ....................... | 525/504 |
| 4,946,925 A | 8/1990 | Strohmayer et al. ........ | 528/122 |
| 5,280,091 A | 1/1994 | Dubowik et al. ........... | 525/504 |
| 5,821,318 A * | 10/1998 | Fischer ....................... | 528/93 |

FOREIGN PATENT DOCUMENTS

GB 1536808 12/1978 ........... C07C/87/40

* cited by examiner

*Primary Examiner*—Marc S Zimmer
(74) *Attorney, Agent, or Firm*—Mary E. Bongiorno; Russell L. Brewer

(57) ABSTRACT

This invention relates to improved polyepoxide resins cured with a mixture of methylene bridged poly(cycloaliphatic-aromatic)amines and a process for preparing such polyepoxide resins as well as to the methylene bridged poly (cycloaliphatic-aromatic)amine compositions and a method of making them. The improvement resides in using a curative (herein referred to as "Heavy MPCA") comprised of the partially hydrogenated condensation product of formaldehyde and aniline or methyl substituted aniline containing a substantial amount (from 35 to 85% by weight, preferably 40 to 60% by weight) of oligomers in the form of 3, 4, 5, 6, 7, 8, 9, 10, 11, 12, 13, 14 and 15 aniline or methyl substituted aniline derivatives.

21 Claims, No Drawings

HYDROGENATION OF METHYLENEDIANILINE HOMOLOGS AND EPOXY RESINS CURED WITH SAME

TECHNICAL FIELD

This invention pertains to mixed methylene bridged poly(cyclohexyl-aromatic)amines and method of making them, and to improved epoxy resins cured with mixed methylene bridged poly(cyclohexyl-aromatic)amines and a process for producing such epoxy resins.

BACKGROUND OF THE INVENTION

Aliphatic and aromatic polyamines have been used in the past for curing epoxy resins. It is well known that the aliphatic amines react at a faster rate with epoxy resins than do aromatic polyamines. Aliphatic polyamines can effect cure at room temperature while aromatic polyamines generally require more rigorous cure conditions or additives which act as accelerators.

Representative patents which describe epoxy resins and the utilization of aromatic and cycloaliphatic amines as curatives, therefore including representative hydrogenation processes are as follows:

U.S. Pat. No. 2,817,644 discloses a process for curing and resinifying polyepoxides by reacting the polyepoxides with hydrogenated aromatic primary or secondary amines. Examples of aromatic amines which could be hydrogenated to form the cycloaliphatic counterparts include p,p'-methylenedianiline, 2,4-diaminotoluene, and the like. The hydrogenated aromatic amines provide epoxy resin products having excellent hardness and excellent resistance to solvents and water.

U.S. Pat. No. 2,981,711 discloses the use of amines as hardening agents for epoxy resins formed by the reaction of a polyglycidylether of a polyhydric phenol with epichlorohydrin. Both aromatic and cycloaliphatic amines are represented and these include para, para'-diaminodiphenylmethane, para, para'-diaminodiphenylpropane, and cycloaliphatic amines include diaminodicyclohexylmethane (often referred to as PACM), diaminodicyclohexylpropane and diaminotricyclohexylmethane.

U.S. Pat. No. 3,959,374 describes a process for the catalytic hydrogenation of methylene-bridged polyphenylamines which contain trace impurities and oligomers. More specifically a crude methylenedianiline feed containing these impurities and oligomers is initially treated with hydrogen in the presence of a nickel containing hydrogenation catalyst prior to hydrogenation in the presence of a ruthenium catalyst. The pretreatment overcomes low yields (52.4%) and long reaction times associated with nickel and cobalt. In the absence of the pretreatment, ruthenium catalysts, although commonly used for hydrogenation of purified methylenedianiline, are not suited for hydrogenation of a methylene dianiline feed containing impurities, e.g., isomeric impurities.

U.S. Pat. No. 4,226,737 and 4,321,353 disclose epoxy curatives which are methylene-bridged polycycloaliphatic polyamines represented by the structural formulas:

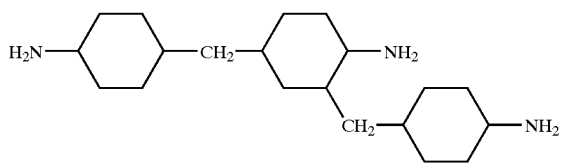

and

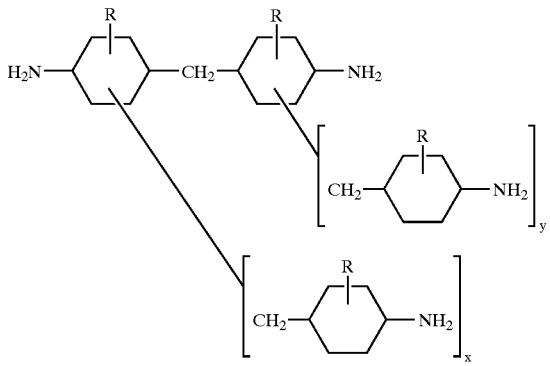

wherein x and y are from 0–2 and the sum of x plus y is from 1 to 4. Typically, the curative consists essentially of from 50 to 75% of the methylene-bridged tricyclohexyltriamine and from 15 to 30% of the tetracyclohexyltetramine. The patentees report that the curing agents overcome substantial problems encountered with prior art amine curatives in that they have lower volatility and reduced toxicological properties. In addition, the patentees report higher glass transition temperatures, and thus improved thermal properties, can be achieved vis-à-vis 1,2-cyclohexanediamine.

U.S. Pat. No. 5,280,091 teaches the partial hydrogenation of three and four ring oligomer condensation products of formaldehyde and aniline or toluidine forms a mixture of methylene bridged poly(cycloaliphatic-aromatic)amines (sometimes referred to as "MPCA") represented by the formula:

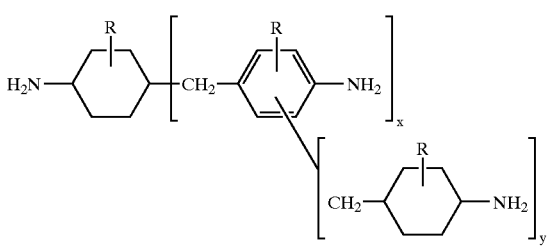

wherein R is hydrogen or methyl, x is 1–3, y is 0–2 and the sum of x and y is from 2 to 4. The hydrogenated product is purified by distillation and used as a curing agent to produce epoxide resins having excellent gloss and water spotting resistance, low toxicity, excellent thermal properties, chemical resistance, and mechanical properties.

British Patent 1,536,808 discloses a process for the hydrogenation of methylene bridged aromatic amines, such as, methylenedianiline (MDA). The patentees suggest that it is well known that the mixed isomeric methylene bridged polycyclohexylpolyamines are useful as curing agents for vicinal epoxides.

SUMMARY OF THE INVENTION

This invention relates to improved polyepoxide resins cured with a mixture of methylene bridged poly (cycloaliphatic-aromatic)amines and a process for preparing such polyepoxide resins as well as to the methylene bridged poly(cycloaliphatic-aromatic)amine compositions and a method of making them. The improvement resides in using a curative (herein referred to as "Heavy MPCA") comprised of the partially hydrogenated condensation product of formaldehyde and aniline or methyl substituted aniline containing a substantial amount (from 35 to 85% by weight, preferably 40 to 60% by weight) of oligomers in the form of 3, 4, 5, 6, 7, 8, 9, 10, 11, 12, 13, 14 and 15 aniline or methyl substituted aniline derivatives. The Heavy MPCA is formed by partially hydrogenating the condensation product, and then, separating the 2-ring hydrogenated derivatives contained therein by distillation. It is the bottoms fraction from that distillation which has low levels (typically less than 10% by weight) of hydrogenated 2-ring component and which has a high concentration of hydrogenated and partially hydrogenated oligomers which is used as the epoxy curing agent or component thereof.

The utilization of the Heavy MPCA, as described above, achieves the common properties cured with the conventional MPCA but also overcomes major problems associated with prior art epoxy curatives and these advantages include:

- an ability to produce epoxy resins cured with amines exhibiting glass transition temperatures (Tg) of ~150° C. minimum;
- an ability to produce epoxy resins having excellent weight per crosslink site (Mc) values, e.g., ~300 or less, typically from 150 to 300 maximum;
- an ability to produce epoxy resins suited for high temperature applications such as filament wound oil field pipe. Conventional epoxy polymers become rubbery and lose strength but, when they are cured with the Heavy MPCA, the epoxy polymers remain glassy and strong in high temperature applications; and,
- an ability to generate epoxy compositions having excellent thermal properties, chemical resistance, and mechanical properties including fracture toughness, flexibility, elongation, strength, etc., required for composites and for structural applications.

DETAILED DESCRIPTION OF THE INVENTION

Polyepoxides which can be cured using the methylene bridged poly(cyclohexyl-aromatic)amines of this invention include those polyepoxides having more than one epoxy group per molecule with the epoxy group typically being a terminal 1,2-epoxy group. The polyepoxides are well known and representative polyepoxides are described in U.S. Pat. No. 3,351,610; U.S. Pat. No. 4,447,586 and U.S. Pat. No. 4,946,925 which are incorporated by reference. Although both liquid and solid polyepoxides can be used, polyepoxides which are liquid are preferred. Examples of polyepoxides which are conventionally used include those which are based upon phenols and aliphatic polyols. Representative phenolic polyepoxides typically used include glycidyl polyethers of polyhydric phenols derived from a polyhydric phenol and epihalohydrin. The resulting polyepoxides generally will have an epoxide equivalent weight ranging from about 100 to 1,000.

Epihalohydrins used in preparing the polyepoxides include epichlorohydrin and epibromohydrin and polyhydric phenols include resorcinol, hydroquinone, di(4-dihydroxyphenyl)methane, commonly referred to as bisphenol F; and, di(4-hydroxyphenyl)propane, commonly referred to as bisphenol A, and novolacs, where the phenolic groups are bridged via methylene groups. Of these polyhydric phenols, those based upon bisphenol A are the most common and preferred in the practice of this invention.

Aliphatic epoxides such as vinylcyclohexene dioxide; 3',4'-epoxy-cyclohexylmethyl-3,4-epoxy-cyclohexane carboxylate and liquid polyglycidyl ethers of polyalcohols such as 1,4-butanediol or polypropylene glycol can also be used.

Other types of polyepoxides which can be cured with the Heavy MPCA and derivatives thereof are glycidyl polyesters prepared by reacting an epihalohydrin with an aromatic or aliphatic polycarboxylic acid. Polyepoxides utilizing glycidyl functionality from a glycidyl amine can also be used. This glycidyl functionality is provided by reacting a polyamine with epichlorohydrin.

The heavier components of the Heavy MPCA distillation mixture or bottoms are represented by the formulas:

Formula 1

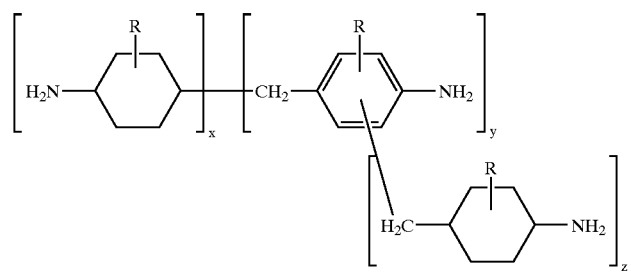

and

Formula 2

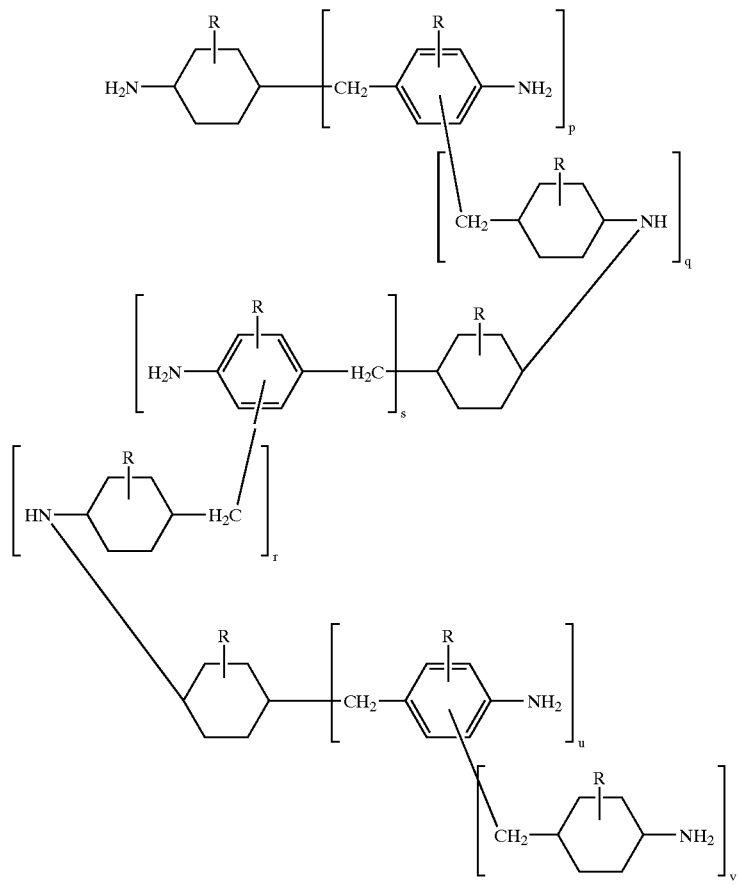

wherein R is hydrogen or methyl, x is 1–13, y is 1–13, z is 1–13, the sum of x, y and z is from 3 to 15, p is 0–14, q is 0–14, the sum of p and q is from 1–14, r is 0–14, s is 0–14, the sum of r and s is from 1–14, u is 0–14, v is 0–14, the sum of u and v is 1–14, and the total number of rings is between 3 and 15.

Although the above formulas represent a large fraction of the components in Heavy MPCA, the Heavy MPCA is further distinguished in terms of the percent of elutable and non-elutable fractions. As with conventional MPCA, the Heavy MPCA also contains an elutable fraction which can be analyzed by gas chromatography. The difference between MPCA and Heavy MPCA here is in the percent of non-elutable fraction. MPCA typically has a level of non-elutable fraction of about 10% by weight or less. Heavy MPCA typically has a substantial non-elutable fraction of at least 15% by weight and typically greater than 20% by weight of the Heavy MPCA fraction. In the above formulas, non-elutables are characterized as having 5 or more rings In an effort to gain an understanding of the composition of heavy MPCA, analysis was done by Matrix Assisted Laser Desorption/Ionization Mass Spectrometry (MALDI). The analyses for MPCA and Heavy MPCA are shown in Table 1 and include both the elutable and non-elutable fractions.

The feedstock for producing the Heavy MPCA composition is based upon MDA or methyl substituted MDA having a high percentage of oligomers, i.e., from 35 to 85% by weight of the feedstock and generally from 40 to 60% by weight. This is in contrast to the methylenedianiline feedstock employed in U.S. Pat. No. 5,280,091 which has from 15 to 30% oligomer content and typically in the range of about 15%.

The Heavy MPCA forming feedstock can be achieved by directly synthesizing the desired feed from aniline or methyl substituted aniline and formaldehyde forming feedstocks having from 35 to 85% by weight oligomer. Common feedstocks are referred to as MDA-15 and MDA-50. MDA-15 and MDA-50 typically will have 85% oligomer and 50% oligomer content, respectively. Alternatively, the Heavy MPCA forming feedstock can be made by mixing different grades of methylene-bridged polyphenylamines and subsequently partially hydrogenating these feeds. For example, one can form a Heavy MPCA forming feedstock by blending a feedstock of lower oligomer content, e.g., MDA-85 or MDA-100 with MDA-15 or MDA-50. In the case of blending, the feedstock contains a portion of high oligomer content material, i.e., the 35 to 85% oligomer. On distillation of the partially hydrogenated product, the heavy component and non-elutable portion remain in the bottoms fraction. The 2-ring material present in the MDA feedstock is removed as an overhead in the distillation process.

Hydrogenation of the crude Heavy MPCA forming feedstock can be effected by well-known processes using a hydrogenation catalyst. Typically, a ruthenium or rhodium catalyst or mixture of the two catalysts is used to effect hydrogenation. Many of the impurities in crude methylenedianiline or di(4-amino-3-methylphenyl)methane act as poisons to hydrogenation catalysts and some precautions must be taken to effect hydrogenation. To convert substantially all of the 2-ring methylenedianiline or di(4-amino-3-methylphenyl)methane to at least partially hydrogenated product, reaction times may extend for a period ranging from one hour to several days. The reaction temperature range is between 130° C. to 210° C., preferably between 170° C. and 200° C. The reaction pressure will range from 500 to 4000 psig (3549 to 27,681 kPa) hydrogen, preferably from 700 to 950 psig (4928 to 6652 kPa). The reaction time varies depending on the amount of impurities in the crude MDA; but if one increases the ruthenium content, one generally can decrease the hydrogenation times (induction period).

Monitoring of the hydrogenation process by sampling is the best method of determining when the desired degree of hydrogenation is obtained. If a low pressure process (700–1500 psig (4928–10,444 kPa)) is used, hydrogenation is deemed complete when the concentration of the 2-ring methylenedianiline is below about 1%, typically below about 0.5% and preferably below about 0.1%. In contrast, if a high pressure process is used, it is capable of complete hydrogenation of the crude aromatic product. In that case, the reaction should be terminated immediately after substantially all of the 2-ring methylenedianiline is converted to fully hydrogenated or partially hydrogenated product and prior to complete hydrogenation of all of the aromatic rings of the oligomer, i.e., the 3 and higher ring components. A problem with both hydrogenation processes, but particularly with the high pressure process, is that higher secondary amine formation can occur when the hydrogenation proceeds to a higher level. Secondary amine formation can affect the properties of the resulting epoxy when cured; e.g., it results in a lower Tg. The hydrogenation of Heavy MPCA forming feedstock produces secondary amines of 4 to 15 rings in size. And, it is preferred that the level of secondary amines in Heavy MPCA is less than 25% by weight. Otherwise, the Tg of the resultant epoxy resin may be adversely effected.

Catalysts suited for hydrogenation are comprised of rhodium and ruthenium on an inert carrier and representative carriers include carbon, calcium carbonate, rare earth oxides, such as cerium, praseodymium, or lanthanum; rare earth oxides or carbonates; alumina; barium sulfate; kieselguhr; pumice; titania; diatomaceous earth; and alkaline earth components such as calcium sulfate, calcium oxide, barium oxide, and barium sulfate. Preferred support materials are alumina and titania with titania being most preferred. The catalyst usually comprises from about 0.01 to 0.25 weight parts metal/weight part of support.

To maintain high activity of the catalyst system in the hydrogenation process it is proposed that at least the rhodium component of the catalyst be alkali moderated. Alkali moderation techniques to produce the catalyst system are well known and the techniques disclosed in U.S. Pat. No. 3,636,108 for the alkali moderation of ruthenium can be utilized for the production of rhodium. Such method is incorporated by reference. Typically, such alkali moderation involves the treatment of the catalyst and support material with an alkali metal hydroxide such as, sodium, lithium or potassium hydroxide or alkali metal alkoxide such as sodium, lithium, or potassium methoxide or ethoxide in an amount to provide from 0.1 to 15% by weight of a basic metal compound calculated as alkali metal. Often, moderation of the catalyst is done prior to reduction of the catalyst with aqueous dilute alkali metal hydroxide during or following metal deposition on the chosen support. Alkali moderation can also be accomplished, in situ, during hydrogenation by including alkali metal hydroxide, alkali metal alkoxide or by the addition of ammonia. For purposes of practicing this invention it is preferred that the catalyst is alkali moderated prior to reduction and maintained in situ with additions of alkali metal hydroxide.

A preferred catalyst system is based upon rhodium and ruthenium. The rhodium to ruthenium ratio is from 12:1 to 1:2, preferably between 2:1 and 4:5. The rhodium to methylene bridged polyphenylamines ratio ranges from 1:10 to 1:3000, preferably about 1:2000. The basic alkali is added in an amount to provide from 0.1 to 15% by weight of a basic metal compound calculated as alkali metal.

One of the surprising aspects in the generation of a Heavy MPCA epoxy curative from MDA-50 is that the elutable portion of the bottoms fraction (after distillation) is quite similar to MPCA obtained in U.S. Pat. No. 5,280,091. For example, the elutable portion of a representative Heavy MPCA, as determined by gas chromatographic analysis with a 300° C. injector temperature, contains the following:

15.5% 2,4-di(4-aminocyclohexylmethyl)cyclohexylamine;

47% 2,4-di(4-aminocyclohexylmethyl)aniline;

4.0% 4,4'-di(4-aminocyclohexylmethyl)dicyclohexylamine and, 23.6% partially hydrogenated trimethylenetetraaniline and analogs thereof.

Recall the elutable portion of an MPCA obtained using MDA-85 as the feedstock in U.S. Pat. No. 5,280,091 substantially free of two ring components and substantially free of non-elutables, as determined by gas chromatographic analysis typically contains:

10–37% 2,4-di(4-aminocyclohexylmethyl)cyclohexylamine;

67–85% 2,4-di(4-aminocyclohexylmethyl)aniline;

0–20% 4,4'-di(4-aminocyclohexylmethyl)dicylohexylamine and,

5–14% partially hydrogenated trimethylenetetraaniline and analogs thereof.

Similarly, the amine hydrogen equivalent of a Heavy MPCA mixture from MDA-50 and MPCA derived from MDA-85, as described above, typically will range from 50 to 60.

The one basic compositional difference between Heavy MPCA and MPCA is in the relative concentration of 5 or more ring components. The non-elutable fraction in Heavy MPCA will vary from 15 to 45% and generally from 20 to 40% by weight (typically around 25% by weight) while MPCA from MDA-85 will have from 5 to 10% of a non-elutable fraction. By non-elutable, it is meant the fraction does not vaporize sufficiently at a temperature of 300° C. for analysis in a GC column. Heavy MPCA samples are highly enriched in 5, 6, 7 and even 8-ring components while the typical MPCA curatives described in U.S. Pat. No. 5,280,091 are mostly comprised of 3 and 4-ring components. By MALDI analysis the ratio of 5 or more ring components to 2–4 ring components in Heavy MPCA is greater than 1:1 and typically is greater than 2:1. In contrast the ratio of 5 or more ring components to 2–4 ring components in conventional MPCA typically is less than 1:1.

The polyepoxides can be cured in conventional manner by effecting reaction with the Heavy MPCA. Typically the amount of Heavy MPCA curative which is reacted with the polyepoxide will range from a level of 0.6 to 1.7 times the stoichiometric or equivalent amount of polyepoxide resin present. Preferably, the level of Heavy MPCA to polyepoxide is from about 0.9 to 1.1 times the stoichiometric amount, stoichiometric being one equivalent weight of epoxide per equivalent weight of amine hydrogen.

Other polyamine curing agents can be used in combination with Heavy MPCA and these include aromatic polyamines such as diethyltoluenediamine, and methylenedianiline; and aliphatic amines such as di(4-aminocyclohexyl)methane (PACM), isophoronediamine, 1,3-xylylenediamine, and polyalkylenepolyamines such as diethylenetriamine and triethylenetetramine and the mixed methylene bridged poly(cyclohexylaromatic)amine, and 4-(4'-aminobenzyl)cyclohexylamine (ABCHA). In many cases the amine functionality for curing is provided by a mixture of Heavy MPCA with an aliphatic amine such as PACM or ABCHA or both.

Conventional accelerators, plasticizers, fillers, glass and carbon fibers, pigments, solvents, etc., used in formulating epoxy coatings, mold compositions, lacquers, etc., can be used. Selection and amount of these additives is at the option of the formulator. The adjustment of cure temperatures and curing times for polyepoxide resins is within the discretion of the formulator. Representative accelerators which may be used, although not mandatory, include: boron trifluoride amine complexes and metal fluoroborate systems, e.g. copper fluoroborate; substituted phenolics, and tertiary amines, such as imidazole, 2,4,6-tri(dimethylaminomethyl)phenol, and benzyldimethylamine.

The following examples are intended to illustrate various embodiments of the invention and are not intended to restrict the scope thereof.

General Hydrogenation Procedure

In this procedure, 58 g of MDA-50 (crude MDA-50 comprised of roughly 50% methylene dianiline, 20% three-ring methylene bridged polyphenylamine, 10% four-ring methylene bridged polyphenylamine and 20% five or more ring methylene bridged polyphenylamine) which was passed through a 2-micron filter, 84 g of tetrahydrofuran (THF) and 0.5 mL of a 10% aqueous LiOH solution were combined with 0.72 g of 4% rhodium on alumina and 0.72 g of 5% ruthenium on alumina in a 300 mL autoclave. The reactor was sealed, purged three times with nitrogen, two times with hydrogen, and pressurized to 820 psig (5755 kPa) hydrogen at 180° C. Given the high ruthenium level in the catalyst system, the reaction had no induction time and took 3.5 hours to complete under a constant hydrogen pressure maintained by the use of a hydrogen ballast tank.

A GC analysis of the elutable portion of the reaction mixture showed 1.3% 2,4-PACM, 44.7% 4,4-PACM (22% trans-trans), 0.3% MDA, 28.6% three-ring, 11.1% four-ring, and 7.1% secondary amine.

The reaction product from the synthesis was vacuum distilled in a fractionating column to remove the two-ring components. The residue contained between 3 and 10% PACM.

EXAMPLE 1

A series of epoxy curatives was generated from a Heavy MPCA feedstock and by blending of various feeds. These samples then were compared to an MPCA epoxy curative, in which the MPCA was based upon U.S. Pat. No. 5,280,091.

Sample 1 was prepared by hydrogenating MDA-50 followed by removal of the 2-ring components, leaving Heavy MPCA as the bottoms fraction.

Sample 2 was prepared by hydrogenating a 1:1 mix of MDA-85 (15% oligomer) and MDA-50 followed by removal of the 2-ring components, leaving Heavy MPCA as the bottoms fraction.

Sample 3 was prepared from a 1:1 mix of MDA-85 and MDA-50. Hydrogenation (carried to a greater extent resulting in higher secondary amine content) was followed by removal of the 2-ring components, leaving Heavy MPCA as the bottoms fraction.

Sample 4 was similar to Sample 3 except that the partially hydrogenated methylenedianiline (ABCHA) was present in greater level while the secondary amine content was lower.

Control Samples 5–8 were prepared from the same MPCA feedstock, i.e., MDA-85 (15% oligomer).

Samples 5, 6, and 7 represent separate sample preparations, heat cures, and DMA analysis. Sample 8 represents a second DMA analysis of sample 7. Sample 9 was prepared from MPCA with a lower amine number.

To aid in differentiating the compositional difference of the non-elutable portion, the non-elutable fraction was analyzed by Matrix Assisted Laser Desorption/ionization Mass Spectrometry (MALDI). This method does not account for the response factors of the various components in the mixture and, therefore, the method has been used to compare relative concentrations of each component between each mixture and not for absolute quantification of components within a mixture.

Evaluation of the epoxy curing agents was effected by Dynamic Mechanical Analysis. Of particular interest were the substantial and unexpected jumps in glass transition temperature and crosslink density as a function of Heavy MPCA composition.

Experimental Conditions

MPCA: amine hydrogen equivalent weight (AHEW)=55. Epoxy Resin: Epon 826, epoxide equivalent weight (EEW)=184. Mix Ratio: 30 parts by weight MPCA per hundred parts by weight epoxy resin.

Each MPCA sample and epoxy resin were preheated to 50°–60° C. prior to mixing. A quantity of 45 g of MPCA+150 g of Epon 826 epoxy resin+1 drop of Byk A 520 air release agent, were hand mixed for 1 minute, centrifuged @ 3,000 rpm for 2 minutes, then poured into 8"×8"×⅛" casting molds. Castings were cured 2 hrs @ 80° C.+3 hrs @ 150° C. then cooled to ambient temperature prior to testing.

Dynamic Mechanical Analysis

Samples were tested for glass transition temperature (Tg), storage modulus (G'), and weight per crosslink site (Mc) by Dynamic Mechanical Analyzer (DMA). Start temperature was −100° C., End temperature was 250° C., and Heating Rate and 10° C./min.

Glass transition temperature=Tan delta maximum

Storage modulus=G' value at Tg+30° C.

Weight per Crosslink Site (Mc)=RTd/G' where: R=gas constant, T=temperature in K°, d=density $Mc = (8.314 \times 10^7)(K°)(1.1)/(G')$ The results are shown in Table 1:

TABLE 1

| Sample | Description | GC Elutable Fraction - Component, % | % Non-elutable | MALDI analysis # of rings | MALDI analysis Wt % | Tg °C. | Mc @ Tg + 30° C. | G' @ Tg + 30° C. |
|---|---|---|---|---|---|---|---|---|
| 1 | Hydrogenated MDA 50 Amine value 8.71 meq/g "HEAVY MPCA" | 2 ring, 4.9<br>3 ring, 62.5<br>4 ring, 3.6<br>ABCHA, 1.5<br>4 ring Sec. Amines, 4.0 | ~25 | 2<br>3<br>4<br>5<br>6<br>7<br>8 | 0.8<br>8.1<br>8.7<br>21.1<br>22<br>25.6<br>13.7 | 176 | 209 | 2.11e8 |
| 2 | Hydrogenated 1:1 mix of MDA-85 and MDA-50 Amine value 8.76 meq/g | 2 ring, 3.8<br>3 ring, 61.7<br>4 ring, 19.0<br>ABCHA, 0.5<br>4 ring Sec. Amines, 12.6 | ~20 | 2<br>3<br>4<br>5<br>6<br>7<br>8<br>9<br>10 | 0.5<br>8.2<br>16.8<br>15.5<br>17.2<br>14.6<br>11.2<br>7.5<br>8.5 | 165 | 278 | 1.56e8 |
| 3 | Hydrogenated 9:1 mix of MDA-85 and MDA-50 High Secondaries Amine value 8.06 meq/g | 2 ring, 7.1<br>3 ring, 47.1<br>4 ring, 8.5<br>ABCHA, 0.1<br>4 ring Sec. Amines, 33.5 | ~15 | 2<br>3<br>4<br>5<br>6<br>7<br>8<br>9<br>10<br>11 | 1.4<br>8.4<br>27.7<br>8.8<br>11.9<br>10.3<br>11.7<br>9.8<br>6.4<br>3.5 | 143 | 298 | 1.25e8 |
| 4 | Hydrogenated 9:1 mix of MDA-85 and MDA-50 High ABCHA Amine value 8.90 meq/g | 2 ring, 0.8<br>3 ring, 69.3<br>4 ring, 11.1<br>ABCHA, 11.0<br>4 ring Sec. Amines, 6.9 | ~15 | 2<br>3<br>4<br>5<br>6<br>7<br>8<br>9<br>10<br>11<br>12 | 0.6<br>12.8<br>11.4<br>10.9<br>13.9<br>13.3<br>11.6<br>11.1<br>8<br>4.6<br>1.8 | 175 | 200 | 2.00e8 |
| 5 | Control MPCA #1 Prep #1 DMA Run #1 Amine value 8.65 meq/g | 2 ring, 9.4<br>3 ring, 54.5<br>4 ring, 7.7<br>ABCHA, 12.7<br>4 ring Sec. Amines, 13.9 | ~10 | 2<br>3<br>4<br>5<br>6<br>7 | 4.6<br>25.6<br>45.3<br>13.8<br>7.1<br>3.6 | 151 | 370 | 1.13e8 |
| 6 | Control MPCA #1 Prep #2 DMA Run #2 Amine value 8.65 meq/g | 2 ring, 9.4<br>3 ring, 54.5<br>4 ring, 7.7<br>ABCHA, 12.7<br>4 ring Sec. Amines, 13.9 | ~10 | 2<br>3<br>4<br>5<br>6<br>7 | 4.6<br>25.6<br>45.3<br>13.8<br>7.1<br>3.6 | 137 | 400 | 1.01e8 |
| 7 | Control MPCA #1 Prep #3 DMA Run #3 Amine value 8.65 meq/g | 2 ring, 9.4<br>3 ring, 54.5<br>4 ring, 7.7<br>ABCHA, 12.7<br>4 ring Sec. Amines, 13.9 | ~10 | 2<br>3<br>4<br>5<br>6<br>7 | 4.6<br>25.6<br>45.3<br>13.8<br>7.1<br>3.6 | 143 | 394 | 9.46e7 |
| 8 | Control MPCA #1 Prep #3 DMA Run #4 Amine value 8.65 meq/g | 2 ring, 9.4<br>3 ring, 54.5<br>4 ring, 7.7<br>ABCHA, 12.7<br>4 ring Sec. Amines, 13.9 | ~10 | 2<br>3<br>4<br>5<br>6<br>7 | 4.6<br>25.6<br>45.3<br>13.8<br>7.1<br>3.6 | 143 | 385 | 9.69e7 |
| 9 | Control MPCA #2 Amine value 8.35 meq/g | 2 ring, 10.8<br>3 ring, 42.1<br>4 ring, 8.0<br>ABCHA, 10.9<br>4 ring Sec. Amines, 16.7 | ~10 | | | 137 | 440 | 9.18e7 |

Observations

As can be noted from the above table, samples 1–4, based on Heavy MPCA, exhibited epoxy resins with a significantly higher Tg, a lower Mc (higher crosslink density), and higher G' values compared to conventional MPCA samples (5–9), i.e., those prepared in accordance with the procedure of U.S. Pat. No. 5,080,291.

Specifically, sample 1, based on the hydrogenated MDA-50, exhibited surprisingly high Tg (>170° C.) and low Mc values, indicating significantly higher crosslinking than the samples using conventional MPCA. It should be noted from the MALDI analysis that the relative ratio of 5 or more ring components to the 2–4 ring components in sample 1 (non-elutable fraction) is 4.7:1. Contrast the MALDI analysis of Example 5 wherein the ratio of 5 or more ring components to 2–4 ring components is about 0.3:1. Typically, the ratio of 5 or more ring components to 2–4 ring components in Heavy MPCA, as determined by MALDI analysis is greater than 1:1 and preferably greater than 2:1.

Samples 3–4, made from MDA blends containing lower levels of the 3 and 4 ring oligomer component in the elutable fraction than sample 1, exhibited significantly lower Mc values in epoxy resins (higher crosslink density) than the conventional MPCA samples 5–9. Samples 3 and 4 do not take into account the higher level of oligomer content in the non-elutable fraction vis-à-vis sample 1. Sample 4 which had a high ABCHA content exhibited a significantly higher Tg and G' and a lower Mc than sample 3 with a lower ABCHA content and a lower amine value. However, both samples exhibited better properties in terms of crosslink density and G' values than samples based upon conventional MPCA curatives of high amine value, e.g. samples 3 and 4 vs. 5–9.

A key feature is that samples 1–4 exhibited higher G' values in the rubbery plateau (Tg+30° C.) indicating the formation of stronger polymers relative to the MPCA cured epoxy samples, i.e., 5–9. For example, samples 5–9 which employed MPCA as the curative, and, having lower non-elutables, resulted in G' values in the e7 range. All of the Heavy MPCA cured samples exhibited a G' value in the e8 range.

With regard to samples 3 and 4 vs. sample 8, clearly the impact of the secondary amines on the overall amine value of the MPCA is significantly smaller for MPCA made from MDA-50 than that made from MDA-85. Note, the values of Mc and G'. Samples 3 and 4 result in a Tg of ~140 to 175° C. while sample 8 had a value of 140° C. with sample 3 having significantly higher secondary amine, e.g., greater than 30% by weight of the elutables (and presumably to a similar extent among the 5 or more ring components).

In applications such as aerospace composites and filament wound epoxy pipe, where high strength at elevated temperatures is desirable, the Heavy MPCA samples based on high oligomer MDA offer significant advantages relative to the commercial samples. Higher crosslink density (i.e. low Mc value) also equates to higher chemical resistance and higher barrier properties in ambient cure formulations.

In summary, it is surprising that the Heavy MPCA curative composition resulted in such significantly higher Tg's, crosslink density, and G' values in epoxy resins than MPCA, given the compositional similarities. It is also surprising that secondary amine dilution in Heavy MPCA does not effect resultant properties in the epoxy resin as much as it does in an MPCA curative.

What is claimed is:

1. In a polyepoxide resin comprising the reaction product of a polyglycidyl ether of a polyhydric alcohol having terminal 1,2 epoxy groups cured with a polyamine curative, the improvement which comprises said curative comprising a methylene bridged poly(cyclohexyl-aromatic)amine mixture herein designated Heavy MPCA, wherein the Heavy MPCA contains 3 ring and higher ring components, represented by the formulas:

Formula 1

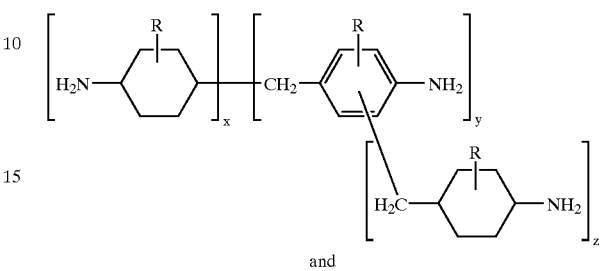

and

Formula 2

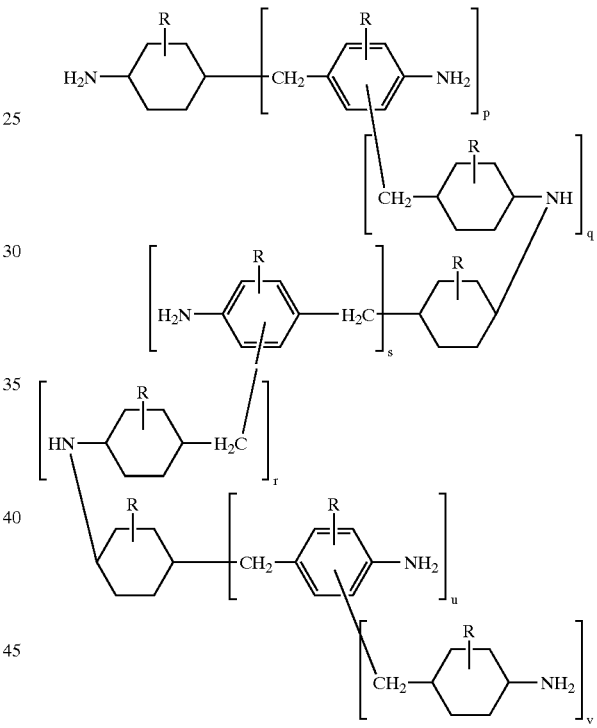

wherein R is hydrogen or methyl x is 1–13, y is 1–13, z is 1–13, the sum of x, y and z is from 3 to 15, p is 0–14, q is 0–14, the sum of p and q is from 1–14, r is 0–14, s is 0–14, the sum of r and s is from 1–14, u is 0–14, v is 0–14, the sum of u and v is 1–14, and the total number of rings is between 3 and 15 and at least 15–40% of said Heavy MPCA is non-elutable as determined by gas chromatography at a 300° C. injector temperature and said Heavy MPCA comprising at least a portion of said polyamine curative.

2. The polyepoxide resin of claim 1 wherein said Heavy MPCA has an amine hydrogen equivalent of 50 to 60.

3. The polyepoxide resin claim 2 wherein the polyglycidyl ether of a polyhydric alcohol is a polyglycidyl ether of bisphenol A or a polyglycidyl ether of bisphenol F.

4. The polyepoxide resin claim 3 wherein R in the formulas is hydrogen.

5. The polyepoxide resin claim 4 wherein the polyglycidyl ether of a polyhydric alcohol is a polyglycidyl ether of bisphenol A.

6. The polyepoxide resin claim 5 wherein at least 20–40% by weight of the Heavy MPCA is non-elutable.

7. In a polyepoxide resin comprising the reaction product of a polyglycidyl ether of a polyhydric alcohol having terminal 1,2 epoxy groups cured with a polyamine curative, the improvement which comprises: said polyepoxide resin at least partially cured with a polyamine curative mixture of partially hydrogenated methylene bridged aniline derivatives, said polyamine curative mixture is formed by hydrogenating a feedstock having as a component thereof a methylene bridged aniline composition having from 35 to 85% oligomer content by weight followed by distillation of the resulting reaction product for removing 2-ring methylene bridged aniline therefrom and recovering a bottoms fraction herein referred to as Heavy MPCA as said polyamine curative mixture.

8. The polyepoxide resin claim 7 wherein the polyglycidyl ether of a polyhydric alcohol is a polyglycidyl ether of bisphenol A or a polyglycidyl ether of bisphenol F.

9. The polyepaxide resin claim 8 wherein the polyglycidyl ether of a polyhydric alcohol is a polyglycidyl ether of bisphenol A.

10. The polyepoxide resin claim 9 wherein at least 20–40% by weight of the Heavy MPCA is a non-elutable fraction as determined by gas chromatography at a 300° C. injector temperature and the secondary amine concentration is less than 20% by weight.

11. The polyepoxide resin of claim 10 wherein the ratio of 5 or more ring components to 2–4 ring components in the non-elutable fraction as determined by MALDI analysis is greater than 1:1.

12. The polyepoxide of claim 10 wherein the ratio of 5 or more ring components to 2–4 ring components in the non-elutable fraction as determined by MALDI analysis is greater than 2:1.

13. The polyepoxide resin of claim 9 wherein the feedstock for the methylene bridged aniline composition has from 40 to 60% oligomer content by weight.

14. In a process for forming an epoxy resin by reacting a polyglycidyl ether of a polyhydric phenol with a polyamine curative wherein the ratio of polyglycidyl ether of a polyhydric phenol to polyamine curative is from 0.6–1.7 amine hydrogens per epoxide equivalent of polyglycidyl ether of a polyhydric phenol, the improvement which comprises utilizing a polyamine curative mixture designated Heavy MPCA, wherein the Heavy MPCA contains 3 ring and higher ring components, represented by the formulas:

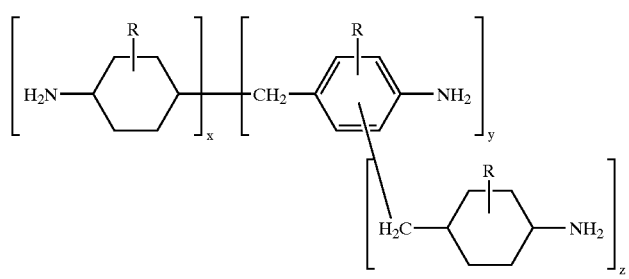

Formula 1 and

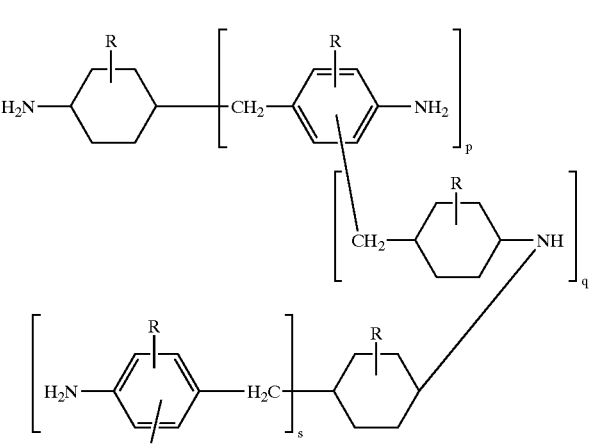

Formula 2

-continued

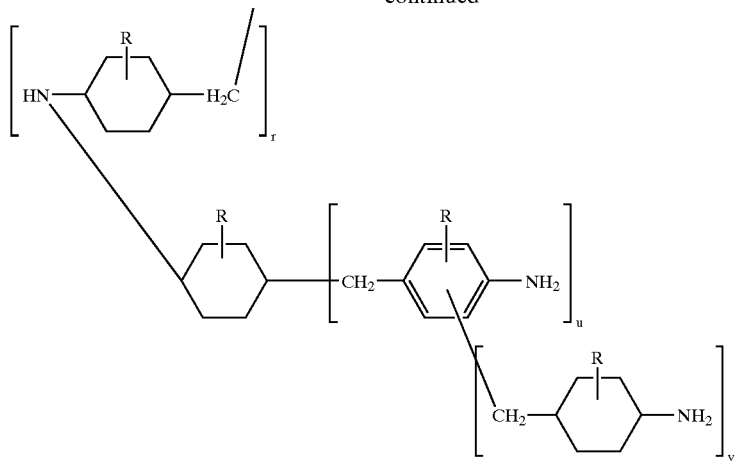

wherein R is hydrogen or methyl, x is 1–13, y is 1–13, z is 1–13, the sum of x, y and z is from 3 to 15, p is 0–4, q is 0–4, the sum of p and q is from 1–14, r is 0–4, s is 0–4, the sum of r and s is from 1–14, u is 0–4, v is 0–4, the sum of u and v is 1–14, and at least a portion of said polyamine curative has a total number of rings between 3 and 15.

15. The process of claim 14 wherein at least 20–40% by weight of the Heavy MPCA employed as said polyamine curative is a non-elutable fraction as determined by gas chromatography at a 300° C. injector temperature and the secondary amine concentration is less than 20% by weight.

16. The process of claim 15 wherein the polyglycidyl ether of a polyhydric phenol is a polyglycidyl ether of bisphenol A or a polyglycidyl ether of bisphenol F.

17. The process of claim 16 wherein R in the formulas is hydrogen.

18. The process of claim 17 wherein the polyglycidyl ether is a polyglycidyl ether of bisphenol A.

19. The process of claim 18 wherein the ratio of 5 or more ring components to 2–4 ring components in the non-elutable fraction as determined by MALDI analysis is greater than 2:1.

20. A methylene bridged poly(cyclohexyl-aromatic)amine mixture containing 3 ring and higher ring components, represented by the formulas:

Formula 1

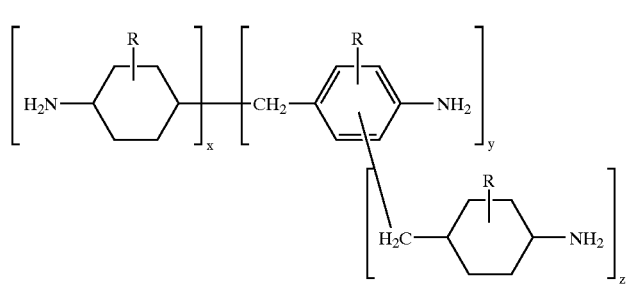

and

Formula 2

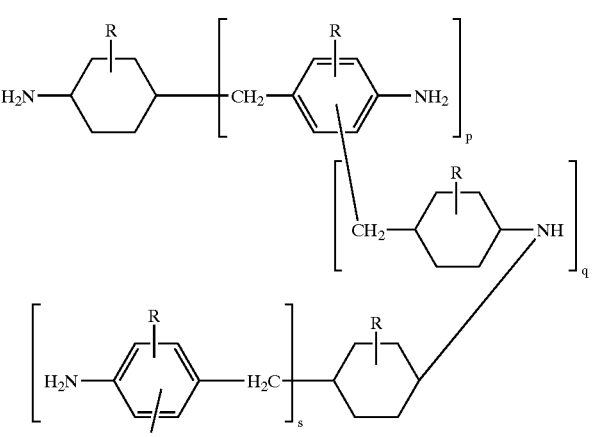

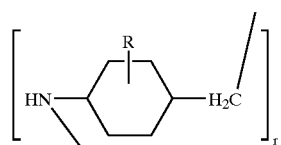

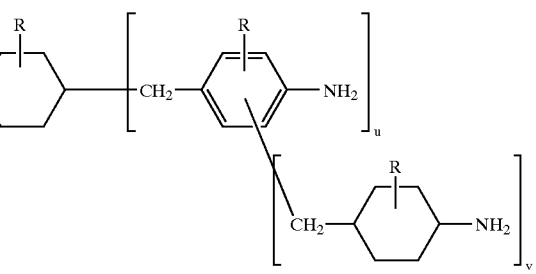

wherein R is hydrogen or methyl, x is 1–13, y is 1–13, z is 1–13, the sum of x, y and z is from 3 to 15, p is 0–14, q is 0–14, the sum of p and q is from 1–14, r is 0–14, s is 0–14, the sum of r and s is from 1–14, u is 0–14, v is 0–14, the sum of u and v is 1–14, and the total number of rings is between 3 and 15 and at least 15–40 % of said mixture is non-elutable as determined by gas chromatography at a 3000° C. injector temperature.

21. In a process for forming a partially hydrogenated methylene bridged aniline mixture by the partial hydrogenation of methylenedianiline having oligomers therein, the improvement which comprises forming a partially hydrogenated methylene bridged aniline mixture containing 3 ring and higher ring components, represented by the formulas:

Formula 1

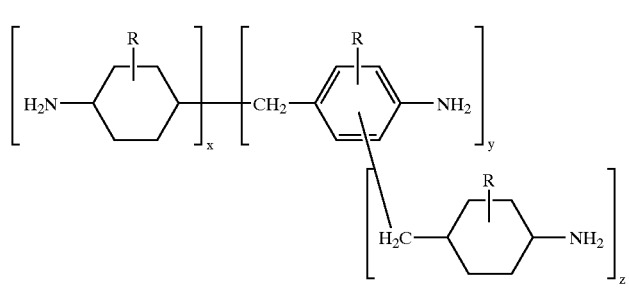

and

Formula 2

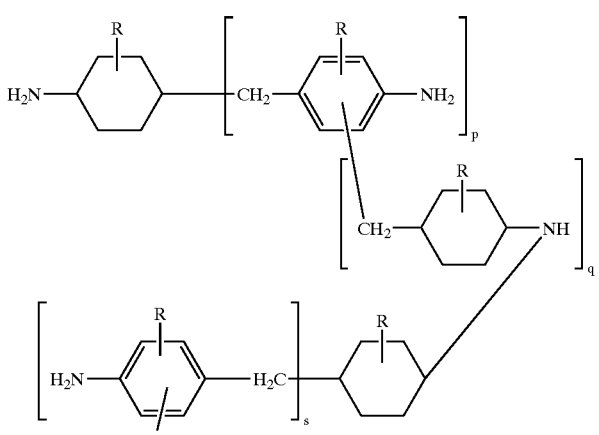

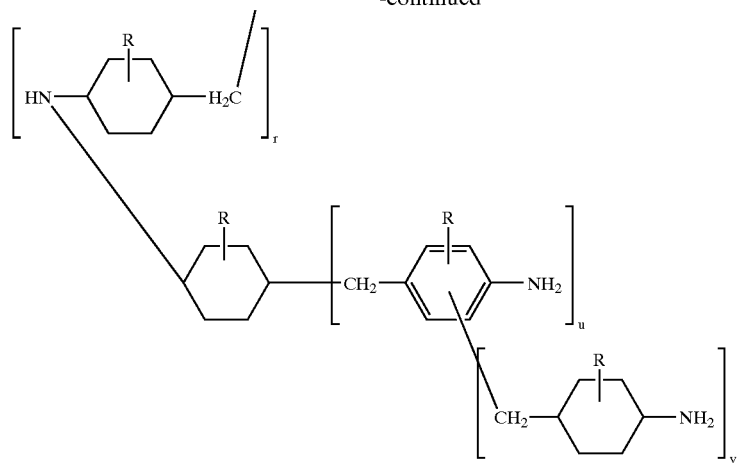
wherein R is hydrogen or methyl, x is 1–13, y is 1–13, z is 1–13, the sum of x, y and z is from 3 to 15, p is 0–4, q is 0–4, the sum of p and q is from 1–14, r is 0–4, s is 0–4, the sum of r and s is from 1–14, u is 0–4, v 0–4, the sum of u and v is 1–14, and the total number of rings is between 3 and 15, and at least 15–40% by weight is a non-elutable fraction as determined by gas chromatography at a 300° C. injector temperature.
* * * * *

UNITED STATES PATENT AND TRADEMARK OFFICE
CERTIFICATE OF CORRECTION

PATENT NO.    : 6,962,964 B2
DATED         : November 8, 2005
INVENTOR(S)   : Ulman et al.

It is certified that error appears in the above-identified patent and that said Letters Patent is hereby corrected as shown below:

Column 19,
Lines 28-29, delete "at a 3000ºC injector temperature" and insert -- at a 300ºC injector temperature --.

Signed and Sealed this

Tenth Day of January, 2006

JON W. DUDAS
*Director of the United States Patent and Trademark Office*